United States Patent [19]
Passariello et al.

[11] Patent Number: 5,938,638
[45] Date of Patent: Aug. 17, 1999

[54] DEVICE FOR THE CONTROLLED INJECTION OF A PROGRAMMABLE QUANTITY OF LIQUID

[76] Inventors: Roberto Passariello, Mogadisciu, 15, Rome, Italy, 00199; Alessandro Bonetti, Via Cartolerie, 30, Bologna, Italy, 40100

[21] Appl. No.: 08/894,897
[22] PCT Filed: Mar. 6, 1996
[86] PCT No.: PCT/EP96/00957
§ 371 Date: Aug. 29, 1997
§ 102(e) Date: Aug. 29, 1997
[87] PCT Pub. No.: WO96/27399
PCT Pub. Date: Sep. 12, 1996

[30] Foreign Application Priority Data

Mar. 6, 1995 [IT] Italy ................................. RM95A0131

[51] Int. Cl.$^6$ .................................................. A61M 5/00
[52] U.S. Cl. ............................................................. 604/131
[58] Field of Search ..................................... 604/131, 132, 604/133, 151, 152, 65–67, 153, 154, 246, 254

[56] References Cited

U.S. PATENT DOCUMENTS

| | | |
|---|---|---|
| 2,193,177 | 3/1940 | Laythorpe . |
| 4,296,500 | 10/1981 | Monties et al. . |
| 4,619,594 | 10/1986 | Moir . |
| 5,303,585 | 4/1994 | Lichte . |

FOREIGN PATENT DOCUMENTS

| | | |
|---|---|---|
| 0 361 662 | 4/1990 | European Pat. Off. . |
| 3632412 A1 | 3/1988 | Germany . |
| 4002268 A1 | 1/1991 | Germany . |
| 43 19 115 A1 | 12/1994 | Germany . |
| 740138 | 11/1955 | United Kingdom . |

Primary Examiner—John D. Yasko

[57] ABSTRACT

The object of the invention is a device (1) for the controlled injection of a programmable quantity of liquid, including means (4) of connection for the container of liquid to be injected, an expulsion chamber (9) for the liquid, equipped with a rotating pump (12, 13, 14) for pumping the liquid from the container and sending it to the usage unit, and means of discharging (16) the liquid, said device (1) being made of a rigid material (FIG. 3).

33 Claims, 4 Drawing Sheets

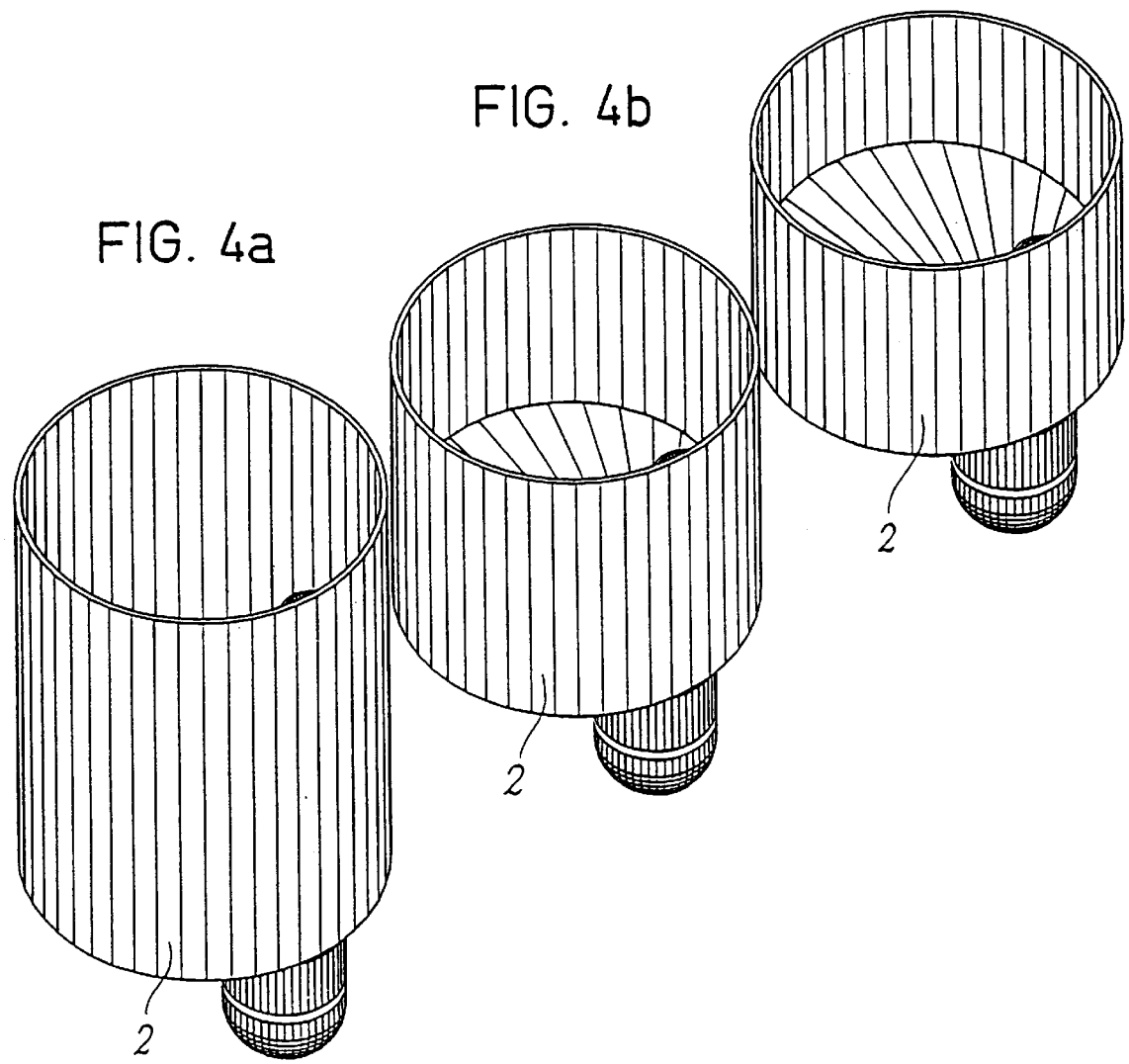

DEVICE FOR THE CONTROLLED INJECTION OF A PROGRAMMABLE QUANTITY OF LIQUID

The invention relates to a device for the controlled injection of a programmable quantity of liquid in diagnostic and therapeutic medical procedures.

More specifically, the invention relates to a device of this type which allows a programmable quantity of liquid to be injected, varying the speed of injection from slow drip infusion up to rapid flow injection.

As is known, the requirement of having a device of this type is felt in nearly all branches of medicine, among which, but not limited to, include intensive care and anesthesiology (infusion of medications and biological liquids), oncology (infusion of chemotherapy), hematology (blood and plasma transfusions), cardiosurgery (heart-lung machine), gastroenterology/anesthesiology/nutrition (parenteral feeding), nephrology (hemodialysis), radiology (injection of contrast medium agents).

It is also true, as in all of the other branches of medicine, that different infusion systems are used according to the specific requirements, especially with regard to the precision of the quantity and speed of injection.

Among those known, without a doubt the simplest infusion system is the "drip".

The drip may be easily regulated according to the height of the flask containing the liquid and the resistance created on the flow path by the gauge of the needle and any compression systems used on the flow control.

In other cases, the infusion system may be equipped with mechanisms to assist the speed of injection by means of pneumatic compression of the liquid container, which in this case obviously cannot be rigid.

The art also uses syringe systems and peristaltic pump systems, of which there are innumerable modes according to the area of usage, the type and quantity of liquid to be injected, the required precision, the minimum speed and the maximum speed of injection.

All users in the area already know that each of these systems has advantages and disadvantages regarding their functionality, technical specifications and cost factors.

The most important requirements in terms of quantity of liquid injected, speed of injection and precision of injection parameters are in the radiology field, where over the years the development of manual, semi-automatic and automatic injectors has shown a significant upsurge.

As a brief historical outline, the need for mechanical injection systems for contrast media in radiology began at the end of the 1920s with the origin of angiographs, mostly thanks to Egas Moniz and Manuel Dos Santos, who, in 1927 and 1929, respectively, were the first to perform cerebral angiographs and abdominal aortographs by percutaneous puncture.

By the middle of the 1950s, angiographs were limited by accessibility, by direct puncture of a few vascular areas, albeit with significant risk, to the need for catheterizations, surgically introducing a catheter by which contrast media were injected, despite the relative toxicity of the contrast agent, the early use of catheters and other angiographic accessories, and the relatively modest use of vascular surgery.

In view of the foregoing, from the end of the 1920s until the 1960s, the demand for mechanical systems for pressurized injection of contrast media was quite low. Pressure injection was indispensable for obtaining a rapid flow of the contrast medium and, consequently, optimal angiographic opaquing of the vascular area being examined.

In 1963, the Swede Seldinger developed a new technique for percutaneous non-surgical introduction of catheters in veins, as a result of which there was a rapid and massive increase in the use of angiographic procedures, which was aided by both the development of rapid automatic seriographs and contrast intensifiers, which were ideal for endovascular guiding of catheters under intensified direct radioscopic control, as well as injectors which were capable of injecting a large quantity of contrast medium in a short time, with a rapid flow rate.

The first mechanical injector made, which was not automatic, was the manual mechanical pump injector, substantially consisting of, with few variations, a steel syringe mounted vertically (or horizontally) on a support, also made of metal, which in turn was attached to a wooden base. The support also held the arm of a lever with a handle, the fulcrum of which was applied to the plunger of the syringe. By pushing the lever, it moved the plunger which then caused the contrast medium to the expelled into a connector tube to the needle or the catheter used in the examination.

This pump system, which was used until 1960–65, had the disadvantage of not being able to control the rate of injection, which was only determined by the force applied by the operator and by the peripheral resistance (viscosity of the contrast agent, gauge of the catheter or needle used, blood pressure).

Mechanical injection systems based upon the force applied by the operator, incidentally, remained in use until very recently.

Between 1955–60, the first automatic injectors appeared, based upon the pump principle but with the advantage, among others, that they could be remote controlled, providing the operator with protection from x-rays.

The first of these injectors was the compressed air injector, in which the plunger of the syringe was depressed, instead of the by the force applied by the operator, by compressed air from a small pump located in the support of the head of the injector (A. Rodriguez-Alvarez, N. Dorbecker—Studies in Angiography: The problem of injection).

This solution allowed, by means of a reducer, the force applied to the plunger of the syringe to be pre-served; the syringe was still made of steel, and some models included a hard rubber gasket.

The quantity of contrast medium to be injected was regulated by means of a mechanical shutoff.

Greater or lesser injection pressure, strongly influenced by peripheral resistance, did not guarantee accurate selection of the injection flow rate.

In view of the above, between the end of the 60s and the beginning of the 70s, the first electromechanical automatic syringe injectors appeared, which are still in use today despite the significant technological progress that followed, still based on mechanical force applied to the syringe plunger.

The syringe, originally made of steel, became disposable plastic by 1975.

Uniformity of flow, which precludes peripheral resistance, is ensured by the control relay with automatic shutoff in case of over-pressure, thus preventing breakage of the catheter.

Numerous studies were performed in order to gain more profound knowledge on the injection characteristics of the various models.

These injectors may be programmed for repetitive injections, to inject before or after x-rays, and, with regard to the flow rate, the quantity of contrast medium injected, the cardiosynchronization of the injection, etc.

The greatest disadvantage of this type of injector is the need to subsequently reload the contrast agent, by aspiration of the container, an awkward and lengthy procedure. According to the number of injections and the quantity of contrast medium used for each injection, it is easy to waste contrast medium or be required to reload during the examination, thus prolonging the procedure.

Using this type of injector, careful attention must be paid to the risk of injecting air bubbles, which accidentally penetrate into the syringe during loading, since they do not have any safety system to control the risk of injecting air instead of contrast agent.

In some models, the head of the injector includes two syringes, in order to have available a larger total quantity of contrast medium and to be able to inject flushing solutions after the first injection of contrast agent.

In order to overcome the disadvantage of reloading the syringe, and the subsequent interruption of the examination to inject the quantity contained in the syringe, besides the limitation of injectors with syringes of 200–300 cc, in the early 1980s a peristaltic pump injector especially for radiology was introduced, particularly for angio-CT (R. Passenello, U. Salvolini, P. Rossi, G. Simonetti and U. Pasquini—Automatic contrast medium injector for computed tomography—Journal of Computer Assisted Tomography—pg. 278–279, April 1980).

This injector aspirates the contrast medium directly from the container during injection, which is continuous.

The injector uses a disposable set of silicon plastic tubing, which is ideal for peristaltic use.

The primary disadvantage of this injector is the maximum rate of injection, which cannot exceed 8–10 cc/second, due to the limited release capacity of the tubing following compression by the rotating component of the peristaltic system.

Based upon prior experience, it is assumed that a theoretically ideas injector should have the following characteristics:

aspiration of the contrast medium directly from the original container, without needing to interrupt the injection or the examination in progress;

injection with a mechanical system composed of a rigid structure, not sensitive to variations in pressure and resistance during injection;

possibility of continuous injection of an amount, variable in quantity from 0, depending on the dimensions of the contrast medium container;

accuracy of the quantity and rate of flow of injection;

suitability of use of each type of contrast medium for each type of radiological examination and for each type of examination: urography, colangiography, computerized tomography angiography, magnetic resonance imaging, etc.

double safety system against injection of air;

disposable transparent components of the injector which are in contact with the contrast medium, which may be used for an entire work shift on many patients, only changing the connection between the injector and the patient for each new patient;

low cost;

ease of use by personnel;

use with non-traditional contrast medium containers suitable for use with the injector.

It is evident that none of the injectors currently known and available fulfill all of the above requirements.

In fact the compressed air injector described above compresses the contrast medium but does not aspirate it.

The peristaltic pump injector "compresses" and "aspirates" but it is mechanically and hydrodynamically not efficient: first, because it is depended on a slower return then the formal round form of the tubing previously compressed during the peristaltic sequence, and secondly, it is not very efficient because of the force of compression on the expendable walls of the injection system and, to a lesser extent, the tubing comprising the set which is subject to peristaltic compression, which necessarily cannot be too rigid.

In view of the foregoing, the applicants have implemented and developed an absolutely innovative solution for a controlled injection device, which allows all of the above characteristics to be fulfilled and dispenses with all of the disadvantages of the prior art.

The solution proposed according to this invention allows a rigid injection system in that it is made of materials which cannot be deformed by the force applied at maximum injection values.

Furthermore, according to the invention, injection is determined by a rotating pump which aspirates the contrast medium and at the same time compresses it for injection during the same rotation of the pump.

The injector consists of an electromechanical and electronic control structure, from which exits a rotating axis connected to the motor that is snapped into a suitable housing located in the "injection block" of the system, which is made of transparent plastic material that is biocompatible and inert with respect to radiological contrast media, ideal for withstanding high flow rate injection pressures even in the presence of high peripheral resistance.

The injection block is disposable and by its design is ideal for performing numerous repetitive injections under typical fluid dynamics conditions of clinical use in various types of radiological examinations in which contrast medium is injected.

The specific purpose of this invention is a device for the controlled injection of a programmable quantity of liquid, including means of connection to the container of liquid to be injected, a liquid expulsion chamber, equipped with a rotating pump for aspirating the liquid from the container and sending it to a usage unit, and a means for evacuating the liquid, this device being made of a rigid material.

According to the invention, the liquid expulsion chamber is preferable made of a body with two identical symmetrical parts along the vertical axis.

Then, according to the invention, the rotating pump includes a rolling sphere with a diameter slightly less than that of the chamber, with a slightly eccentric axis of rotation, and is equipped with at least one movable paddle, the sphere and the movable paddle, of which there is at least one, being resistant to high pressure.

According to the invention, the paddle, of which there is at least one, is loosely inserted in an opening in the rolling sphere.

According to a preferred embodiment of the device according to the invention, between the liquid expulsion chamber and the means of connection for the liquid to be injected there may be a reservoir for the liquid, the dimensions of which may vary according to need.

The reservoir may be equipped with a safety system, in particular a floating sphere within a tube, for opening and closing the passage of air and/or liquid.

The means of connecting the liquid container may be equipped, according to the invention, with a snap-to-connect mechanism for opening and closing the passage of air and liquid.

Between the means of connection of the liquid container and the expulsion chamber of the reservoir and possibly between the reservoir and the expulsion chamber, there are hermetic sealing means.

Then, according to the invention, the means of evacuating the liquid may be equipped with means for eliminating air bubbles, in particular a spherical dome with a release hole, closed off by an evacation chamber, in which a spastic sphere floats.

According to the invention, safety and control systems may be included, in particular to prevent programming the injection without having input the relative date regarding the quantity of liquid in the container, to prevent injection of a quantity in excess of the quantity programmed, and to prevent operation of the rotating pump when empty.

It preferably be equipped with an ultrasound control system.

A description of this invention follows as an illustration of, but not limited to, the preferred embodiment, with special reference to the attached figures, in which:

FIG. 4a, 4b and 4c are views in perspective of various reservoirs for the device in FIG. 1.

We must first indicate that, although in various parts of this description we refer to a device according to the invention used in the radiological field to introduce a contrast medium, the device may find valid applications in any medical field in which an infusion system is necessary.

Figure 1:
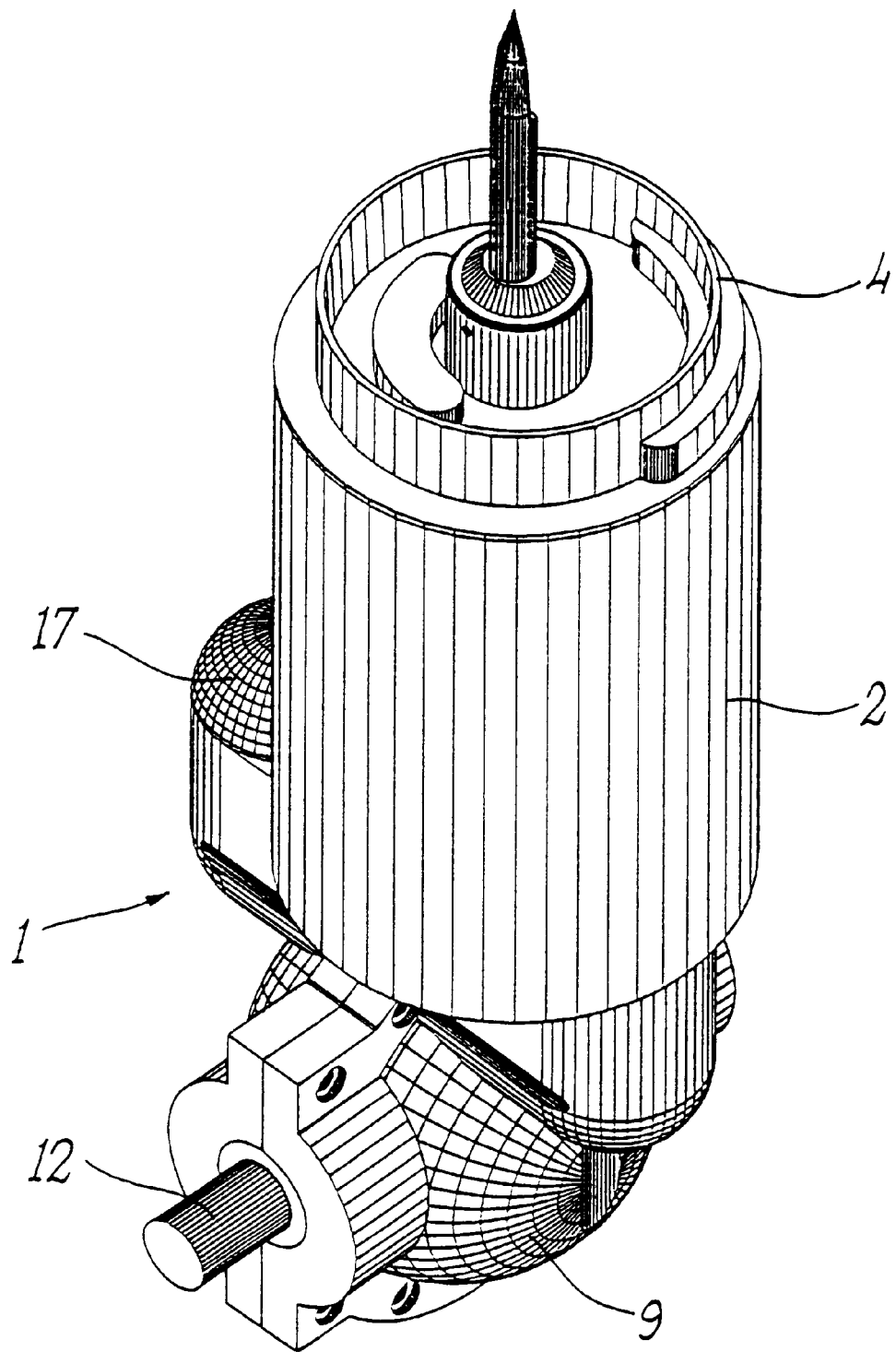
FIG. 1 is the first view in perspective of an embodiment of the device according to the invention.
Figure 2:
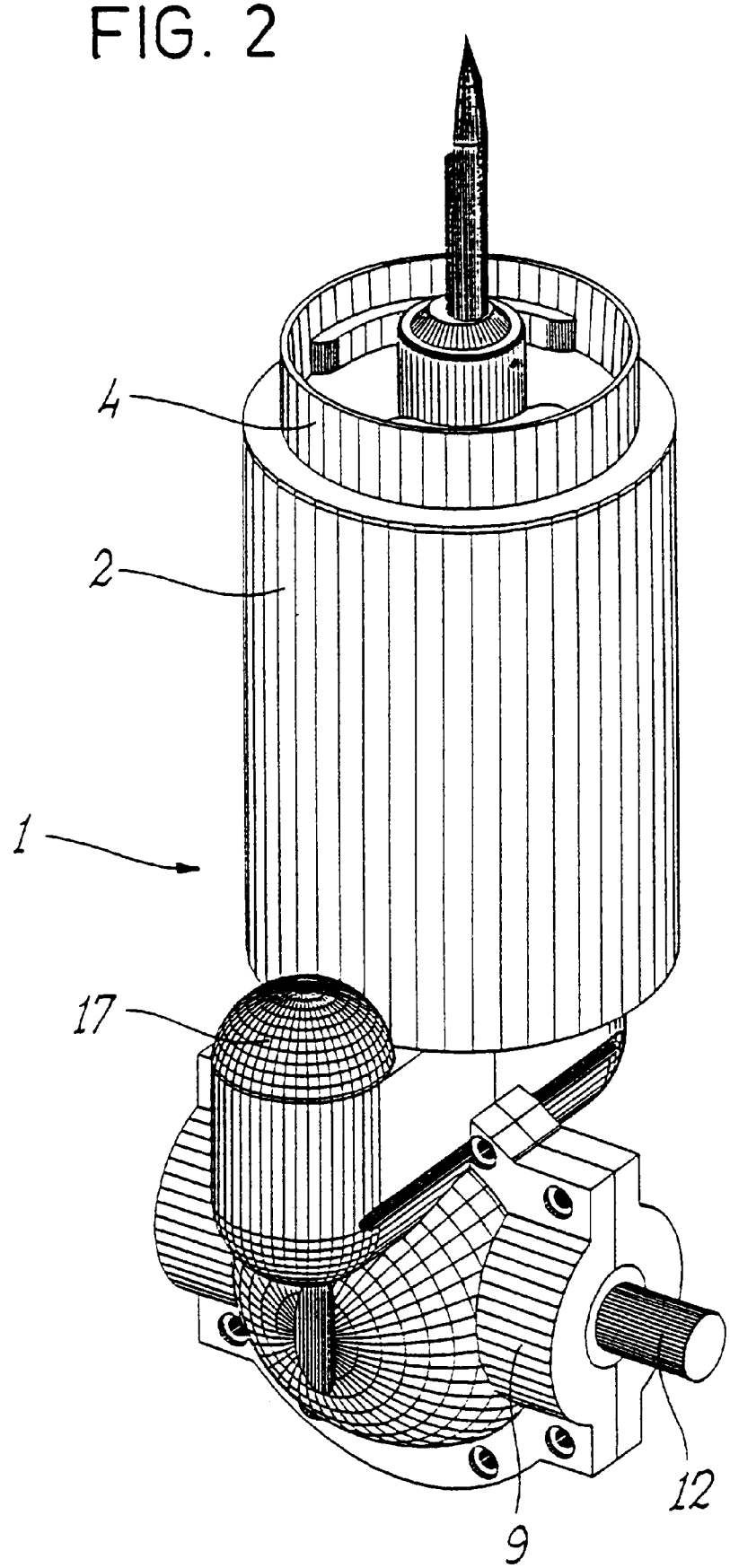
FIG. 2 is the second view in perspective of an embodiment of the device according to the invention.
Figure 3:
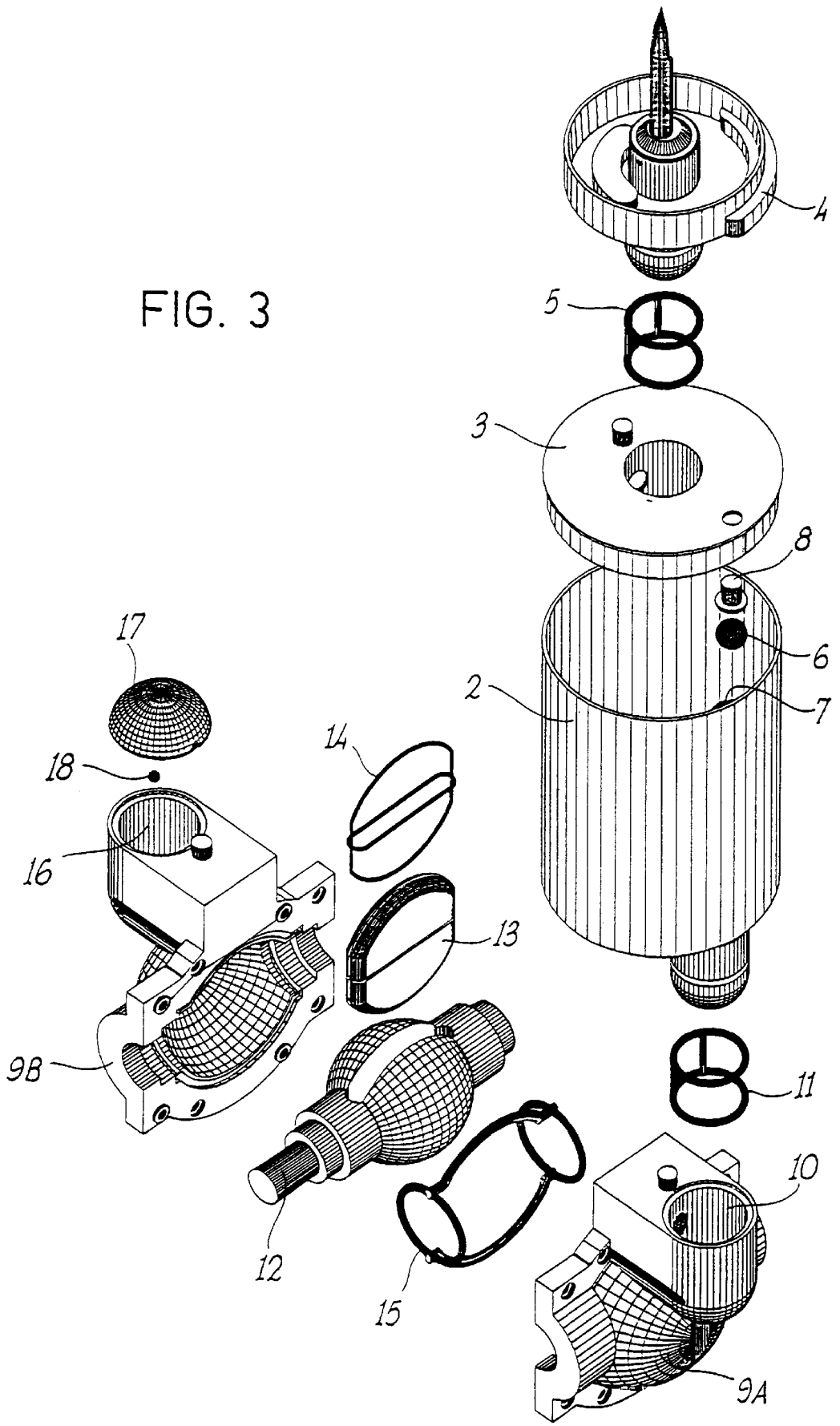
FIG. 3 is an expanded view of the device in FIG. 1.

With regard to FIGS. 1 to 3, a device 1 is illustrated for the controlled injection of a programmable quantity of liquid according to the invention that includes a reservoir 2, in the specific case 150 (cc?), equipped with a cover 3.

Above the cover 3 is a puncture device 4, installed with a suitable gasket 5.

The connection between the puncture device 4 and the cover 3 is made by twisting and snapping into place, as is illustrated in the drawing.

Inside the reservoir 2 are a rubber sphere 6, loosely fitting into a seat 7 and a push-button 8 for unlocking the sphere, the function of which will be fully described below.

Underneath, reservoir 2 is connected to the body of the pump by means of insertion into opening 10, by means of a gasket 11, identical to gasket 5.

Thus, it is also possible to connect the puncture element 4 directly to the pump body 9, as it is possible to connect to the pump body 9 the contrast medium container made to suitably function with the injection system.

The pump body 9 consists of two halves, 9a and 9b, which are identical and thus can be made from the same die.

Between the two halves 9a and 9b of the pump body 9 is a paddle holder shaft 12, equipped with a rotating paddle 13.

On the paddle 13 and the shaft 12 are gaskets 14 and 15, respectively, specially designed to provide the maximum resistance in all phases of infusion.

In opening 16 of half 9b of the pump body 9 is a dome 17, with a release opening which acts in conjunction with a rubber sphere 18 measuring 3 mm.

FIGS. 4a, 4b and 4c illustrate reservoir 2 with various dimensions, all of which can be used with device 1 according to the invention.

In the solution with reservoir 2, the dimensions of which may be selected according to need, according to the type of drug and the type of application, there is a device 1 which is on the assembled version as illustrated in FIGS. 1 and 2.

Above the puncture element 4 is the container, which is rotated in such a manner as to unblock the opening down into the liquid reservoir.

After the inflow of the liquid, the sphere 6 begins to exit in such a way that when reservoir 2 is full it blocks the liquid from entering.

The liquid may then be aspirated by the action of the pump, which transfers it into opening 16 and makes it exit through the injector (not illustrated).

When the liquid in the reservoir is finished, the sphere 6 no longer floats and blocks the passage to the pump which otherwise would aspirate air.

Sphere 6, which initially controlled the filling of reservoir 2, ensuring that no air was inside, moves in the opposite direction, thus impeding the passage of air through tube 7. In the device according to the invention, three primary components may be identified.

The first is the aspiration chamber for the contrast medium or other substance, consisting of an opening of variable dimensions according to the container 2 used, which varies according to the type of use of device 1 according to the invention.

The opening overlaps the injection block and is an integral part thereof; it is the hermetic seal and, above it, there is a puncture element 4 which punctures the rubber tops of the containers of various contrast media, such as those used in uroangiographic contrast media overflows. The puncture element 3 (sic) is equipped with a rotating mechanism which allows the passage of air or contrast medium to be opened or closed.

According to the type of examination and contrast medium used, different types of openings may be used as accessories, the dimensions of which vary. The smallest has a low cc opening; this solution is suitable for examinations which use a modest and constant quantity of contrast medium (urography, magnetic resonance imaging, selective arteriography). in this event, the contrast medium container (not illustrated) is connected directly to the aspiration/injection chamber below.

The opening has larger dimensions with a reservoir of 50 or 100 cc or more in capacity (see FIG. 4a, 4b and 4c) when examinations are to be performed which use greater, variable quantities of contrast medium, introduced with multiple injections (multi-site arteriography, computerized tomography, echography).

In these cases, the reservoir is divided vertically into a larger and smaller chamber connected at the lower part of the reservoir, where the contrast medium overflow opening to the rotating system is also located. By the principle of connecting containers, once the chamber is full, the contrast medium levels off within the two chambers.

The smaller chamber is made of a cylinder in which there is a floating sphere 6 made of a plastic material, the function of which is to block the contrast medium overflow opening when the reservoir is empty. Operation of the pump when empty without a contrast medium container being connected to the reservoir causes negative pressure in the reservoir, which acts as a mechanism to aspirate the contrast medium, once a contrast medium container is connected to the reservoir.

Henceforth, with operation of the rotating pump 9, 10, there is simultaneous compression and injection of the contrast medium toward the point of exit of the injector and aspiration of the contrast medium from the point of entry, which corresponds to the puncture element 3 (sic) positioned on the contrast medium container.

The flow of the contrast medium is always in one direction and may be continuous, by the reservoir supplying the containers. When the quantity of the programmed injection exceeds the quantity of contrast medium contained in the reservoir and the containers connected to the reservoir, emptying the reservoir of all of the contrast medium contained, the ball floating on the contrast medium covers the exit opening of the contrast medium, blocking the contrast medium overflow.

The quantity of contrast medium contained in the reservoir is, however, always shown by the system electronics with a manual mechanism and an automatic mechanism (not illustrated). The manual mechanism consists of a display of the quantity of contrast medium available keyed in by the operator at the beginning of the examination and changed during the examination by the injector as programmed from time to time.

The automatic system consists of an ultrasound reader connected to the reservoir, which reads the progressive emptying of the reservoir.

The second component of the device according to the invention consists of a rotating paddle 13 and the contrast medium expulsion chamber.

The contrast medium expulsion chamber is a spherical opening in which a sphere rolls, the diameter of which is slightly smaller than that of the chamber, the axis of rotation of which is in a slightly eccentric position with respect to the axis of the opening. In a transversal slot in the sphere is a paddle 13, the diameter of which corresponds to that of the opening, and the two ends of which may re-enter the sphere are equipped with a high pressure gasket 14 at the end.

The asymmetry of rotation of the sphere in the opening determines the progressive exit cycle of the end of the paddle 13, which comes through the chamber and re-enters the sphere at the opposite end. Due to the asymmetry of rotation of the sphere, the uniform spherical nature of the opening in which it rolls and the slightly greater diameter of the opening with respect to the sphere in the opening during rotation of the sphere and the paddle 13, a compression and expulsion chamber is created for the contrast medium, which is crescent-shaped with a volume of approximately 5 cc.

Consequently, for each 360° rotation of the sphere in the opening, one side aspirates and the other expels 5 cc of contrast medium, and within one second the resulting injection rate is 5 cc/second.

The third basic component of the device according to the invention is the air bubble trap at the exit of the system.

At the exit of the contrast medium expulsion chamber is a small reservoir or opening 16 for the contrast medium to exit down, whereas at the top of the reservoir is a small release hole for the air to exit in the injector refilling phase in a dome 17.

Inside there is a floating ball 18, the function of which is to block the release hole when the reservoir is refilled with contrast medium and at the same time emptied of air, and to close the contrast medium overflow hole when the quantity of contrast medium inside with reservoir is exhausted.

The device 1 according to the invention is also equipped with control and safety systems because, in an injection system based on the simultaneous aspiration/compression of contrast medium, the greatest danger is the inadvertent injection of gas into the vascular system.

The device 1 according to the invention is protected from this risk by various control and safety mechanisms.

First, the device 1 does not allow any contrast medium to be programmed if the operator has not keyed in, at the beginning of the examination, the quantity of contrast medium contained and available in the container.

Furthermore, the device does not allow programming the injection of quantities exceeding the quantity of contrast medium available or remaining.

When the rotating pump continues to operate, aspirating air into an empty contrast medium container, this air does not enter into the compression chamber of the injector block but rather goes above the contrast medium which fills the lower part of the reservoir, when the reservoir has a capacity of 50–100 cc. This danger is typically noted when the type of examination and the procedure system require numerous repetitive injections of large, variable quantities of contrast medium.

This risk is not present when the container is connected directly to the pump, without a reservoir in between, because the type of examination has entailed adoption of this solution.

In the case of the above solution, the contrast medium level reader with the ultrasound mechanism in the reservoir prevents an injection quantity exceeding that in the reservoir from being programmed, unless the system is actually reset by the operator after replacing an empty container.

When the ultrasound reading mechanism records a drop in contrast medium level inside the reservoir of around zero, because the contrast medium was exhausted and not supplied in the meantime by an empty container, the injection is interrupted, allowing the operator to either suspend the examination, if it was nearing the end, or to replace the empty container with a full one in order to proceed with the examination.

In the event that the above safety mechanisms do not work and the paddle 13 continues to rotate within the opening, exhausting the contrast medium, the ball 6 which floats on the contrast medium obstructs the contrast medium exit opening.

In the event of penetration of air into the contrast medium aspiration/expulsion chamber, the rapid reduction in rotation resistance of the paddle 13 causes an immediate shutdown of the turning of the motor.

Then, if all of the above mechanisms fail to be activated and efficient and air is expelled into the injection opening, the penetration of the air injected by the system in the bubble trap causes a progressive drop in the level of contrast medium and consequently of the ball floating on the contrast medium, until the ball is lodged in the exit of the contrast liquid, thus closing it.

Furthermore, the formation of small bubbles of air in the system and the penetration of bubbles in the trap causes the contrast medium level to drop in the chamber and consequently that of the ball floating on the contrast medium; in this event, the air, due to the difference in resistance, exits the release hole at the top of the chamber.

This invention has been described for illustrative but not limitative purposes, according to its preferred embodiment, but it is to be understood that variations and/or modifications may be made by experts in the field, without departing from the relative scope of the invention, as defined in the attached claims.

We claim:

1. An apparatus for controlled injection in diagnostic and therapeutic medical procedures of a programmable quantity of liquid, the apparatus comprising a connection device in communication with a container of the liquid to be injected, a liquid expulsion chamber in communication with the connection device, the liquid expulsion chamber comprising a rotating pump for aspirating the liquid from the container and sending the liquid to a usage unit, and means for evacuating the liquid, the connection device comprising a snap-on rotating mechanism for opening and closing a passage of air and liquid.

2. The apparatus of claim 1 wherein the liquid expulsion chamber comprises a body having two identical symmetrical parts.

3. The apparatus of claim 1 wherein the rotating pump comprises a rolling sphere having a diameter slightly less than that of the chamber and a slightly eccentric axis of rotation, equipped with], and at least one movable paddle, said sphere and said paddle being associated with resistance means for high pressure.

4. The apparatus of claim 3 wherein the at least one paddle is loosely arranged in an opening in the rolling sphere.

5. The apparatus of claim 1, further comprising a reservoir for the liquid disposed between the connection device and the liquid expulsion chamber.

6. The apparatus of claim 5 wherein the reservoir comprises a safety system for opening and closing the passage of air and/or liquid, the safety system comprising a floating ball in a tube.

7. The apparatus of claim 1, further comprising means for hermetic sealing disposed between the connection device and the liquid expulsion chamber.

8. The apparatus of claim 1 wherein the means of evacuating the liquid comprises means for eliminating air bubbles.

9. The apparatus of claim 8 wherein the means for eliminating air bubbles comprises a dome including a floating sphere therein, the dome defining an opening for liquid overflow and an air release opening.

10. The apparatus of claim 1, further comprising safety and control systems to prevent programming the injection without having input the date relative to quantity of liquid in the container, to prevent injection of quantities of liquid exceeding that programmed, and to prevent operation of the rotating pump when empty.

11. The apparatus of claim 10 wherein the control system comprises an ultrasound control system.

12. An apparatus for controlled injection in diagnostic and therapeutic medical procedures of a programmable quantity of liquid, the apparatus comprising a connection device in communication with a container of the liquid to be injected, a liquid expulsion chamber in communication with the connection device, the liquid expulsion chamber comprising a rotating pump for aspirating the liquid from the container and sending the liquid to a usage unit, means for evacuating the liquid and means for hermetic sealing disposed between the connection device and the liquid expulsion chamber.

13. The apparatus of claim 12 wherein the liquid expulsion chamber comprises a body having two identical symmetrical parts.

14. The apparatus of claim 12 wherein the rotating pump comprises a rolling sphere having a diameter slightly less than that of the chamber and a slightly eccentric axis of rotation, and at least one movable paddle, said sphere and said paddle being associated with resistance means for high pressure.

15. The apparatus of claim 14 wherein the at least one paddle is loosely arranged in an opening in the rolling sphere.

16. The apparatus of claim 12, further comprising a reservoir for the liquid disposed between the connection device and the liquid expulsion chamber.

17. The apparatus of claim 16 wherein the reservoir comprises a safety system for opening and closing a passage of air and/or liquid, the safety system comprising a floating ball in a tube.

18. The apparatus of claim 12 wherein the connection device comprises a snap-on rotating mechanism for opening and closing the passage of air and liquid.

19. The apparatus of claim 12 wherein the means of evacuating the liquid comprises means for eliminating air bubbles.

20. The apparatus of claim 19 wherein the means for eliminating air bubbles comprises a dome including a floating sphere therein, the dome defining an opening for liquid overflow and an air release opening.

21. The apparatus of claim 12, further comprising safety and control systems operable to prevent programming the injection without having input the date relative to quantity of liquid in the container, to prevent injection of quantities of liquid exceeding that programmed, and to prevent operation of the rotating pump when empty.

22. The apparatus of claim 21 wherein the control system comprises an ultrasound control system.

23. An apparatus for controlled injection in diagnostic and therapeutic medical procedures of a programmable quantity of liquid, the apparatus comprising a connection device in communication with a container of the liquid to be injected, a liquid expulsion chamber in communication with the connection device, the liquid expulsion chamber comprising a rotating pump for aspirating the liquid from the container and sending the liquid to a usage unit, means for evacuating the liquid and safety and control systems operable to prevent programming the injection without having input the date relative to quantity of liquid in the container, to prevent injection of quantities of liquid exceeding that programmed, and to prevent operation of the rotating pump when empty.

24. The apparatus of claim 23 wherein the liquid expulsion chamber comprises a body having two identical symmetrical parts.

25. The apparatus of claim 23 wherein the rotating pump comprises a rolling sphere having a diameter slightly less than that of the chamber and a slightly eccentric axis of rotation, and at least one movable paddle, said sphere and said paddle being associated with resistance means for high pressure.

26. The apparatus of claim 25 wherein the at least one paddle is loosely arranged in an opening in the rolling sphere.

27. The apparatus of claim 23, further comprising a reservoir for the liquid disposed between the connection device and the liquid expulsion chamber.

28. The apparatus of claim 27 wherein the reservoir comprises a safety system for opening and closing a passage of air and/or liquid, the safety system comprising a floating ball in a tube.

29. The apparatus of claim 23 wherein the connection device comprises a snap-on rotating mechanism for opening and closing the passage of air and liquid.

30. The apparatus of claim 23 wherein the means of evacuating the liquid comprises means for eliminating air bubbles.

31. The apparatus of claim 30 wherein the means for eliminating air bubbles comprises a dome including a floating sphere therein, the dome defining an opening for liquid overflow and an air release opening.

32. The apparatus of claim 23, wherein the control system comprises an ultrasound control system.

33. The apparatus of claim 23, further comprising means for hermetic sealing disposed between the connection device and the liquid expulsion chamber.

\* \* \* \* \*